United States Patent
Zhang

(10) Patent No.: US 7,900,499 B2
(45) Date of Patent: Mar. 8, 2011

(54) IMPACT TESTING APPARATUS

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 0 days.

(21) Appl. No.: 12/334,533

(22) Filed: Dec. 15, 2008

(65) Prior Publication Data

US 2010/0024519 A1    Feb. 4, 2010

(30) Foreign Application Priority Data

Jul. 30, 2008  (CN) .......................... 2008 1 0303219

(51) Int. Cl.
*G01N 3/303*  (2006.01)
*G01N 3/30*  (2006.01)
(52) U.S. Cl. ........................ 73/12.13; 73/12.01; 73/12.09
(58) Field of Classification Search .................. 73/11.01, 73/11.03, 12.01, 12.04, 12.06, 12.13
See application file for complete search history.

(56) References Cited

U.S. PATENT DOCUMENTS

| | | | | |
|---|---|---|---|---|
| 3,266,289 A * | 8/1966 | Stamy | ........................... | 73/12.13 |
| 3,277,693 A * | 10/1966 | D Amato et al. | ............. | 73/12.09 |
| 3,495,307 A * | 2/1970 | Metz | .............................. | 411/555 |
| 3,859,841 A * | 1/1975 | Evans et al. | .................. | 73/12.13 |
| 4,408,922 A * | 10/1983 | D'Alessio | ....................... | 403/12 |
| 4,969,784 A * | 11/1990 | Yanke | ............................ | 410/104 |
| 5,595,123 A * | 1/1997 | Tao et al. | ....................... | 105/396 |
| 5,690,460 A * | 11/1997 | Attanasio | ...................... | 411/551 |
| 6,523,391 B1 * | 2/2003 | Knox et al. | ................... | 73/12.06 |
| 7,192,103 B2 * | 3/2007 | Hamilton | ................... | 312/334.5 |
| 7,631,856 B2 * | 12/2009 | Zhang et al. | ................. | 269/48.1 |
| 2004/0016712 A1* | 1/2004 | Hamilton | ...................... | 211/134 |
| 2004/0257805 A1* | 12/2004 | Lee et al. | ...................... | 362/226 |
| 2005/0016256 A1* | 1/2005 | Ishikawa | ...................... | 73/12.13 |
| 2009/0008848 A1* | 1/2009 | Zhang et al. | ..................... | 269/50 |
| 2009/0031783 A1* | 2/2009 | Fukushima et al. | ......... | 73/12.06 |
| 2009/0235718 A1* | 9/2009 | Fox | .............................. | 73/12.06 |

FOREIGN PATENT DOCUMENTS

CN       2837824 Y       11/2006

* cited by examiner

*Primary Examiner* — Lisa M Caputo
*Assistant Examiner* — Jonathan Dunlap
(74) *Attorney, Agent, or Firm* — Zhigang Ma

(57) ABSTRACT

An impact testing apparatus for includes a workbench, a bracket defining a vertical passage, a hammer slidably received in the passage of the bracket, a fastening mechanism slidably mounted to the bracket and an anvil for supporting a workpiece to be tested. The workbench includes a horizontal platform. The bracket is arranged over the platform. The fastening mechanism is configured to be selectively fixed to different heights of the bracket relative to the platform, and includes a retaining member capable of being biased between a fist position to hold the hammer and a second position to release the hammer. The anvil is disposed on the platform and aligns with the hammer.

13 Claims, 9 Drawing Sheets

IMPACT TESTING APPARATUS

BACKGROUND

1. Technical Field

The present disclosure relates to testing apparatuses and, more particularly, to a testing apparatus for performing an impact test of a manufactured workpiece.

2. Description of Related Art

Generally, most manufactured workpieces are required to have sufficient durability against destructive acts from outside, thus after the workpieces are manufactured, impact tests are usually performed thereupon via impact testing apparatuses. An ordinary impact testing apparatus includes a horizontal workbench, an anvil with an opening defined therein placed on the workbench, a pin, a hollow sleeve defining a passage and a plurality of slots at a wall of the sleeve, and a hammer slidably received in the passage of the sleeve. In use, a workpiece to be tested is placed on the anvil. The sleeve is vertically located above the workpiece with the passage coaxially aligning with the opening of the anvil. The hammer is lifted to a predetermined height via the pin being inserted through the hammer to engage in a corresponding slot of the sleeve, wherein the hammer aligns with the opening of the anvil. The pin is released to make the hammer fall toward the anvil, to impact the workpiece. Thus, durability against destructive acts of the workpiece can be obtained. However, assembling or disassembling the hammer via the pin is inconvenient, and the hammer may only be lifted at limited positions, according to the plurality of slots.

DETAILED DESCRIPTION

Figure 1:
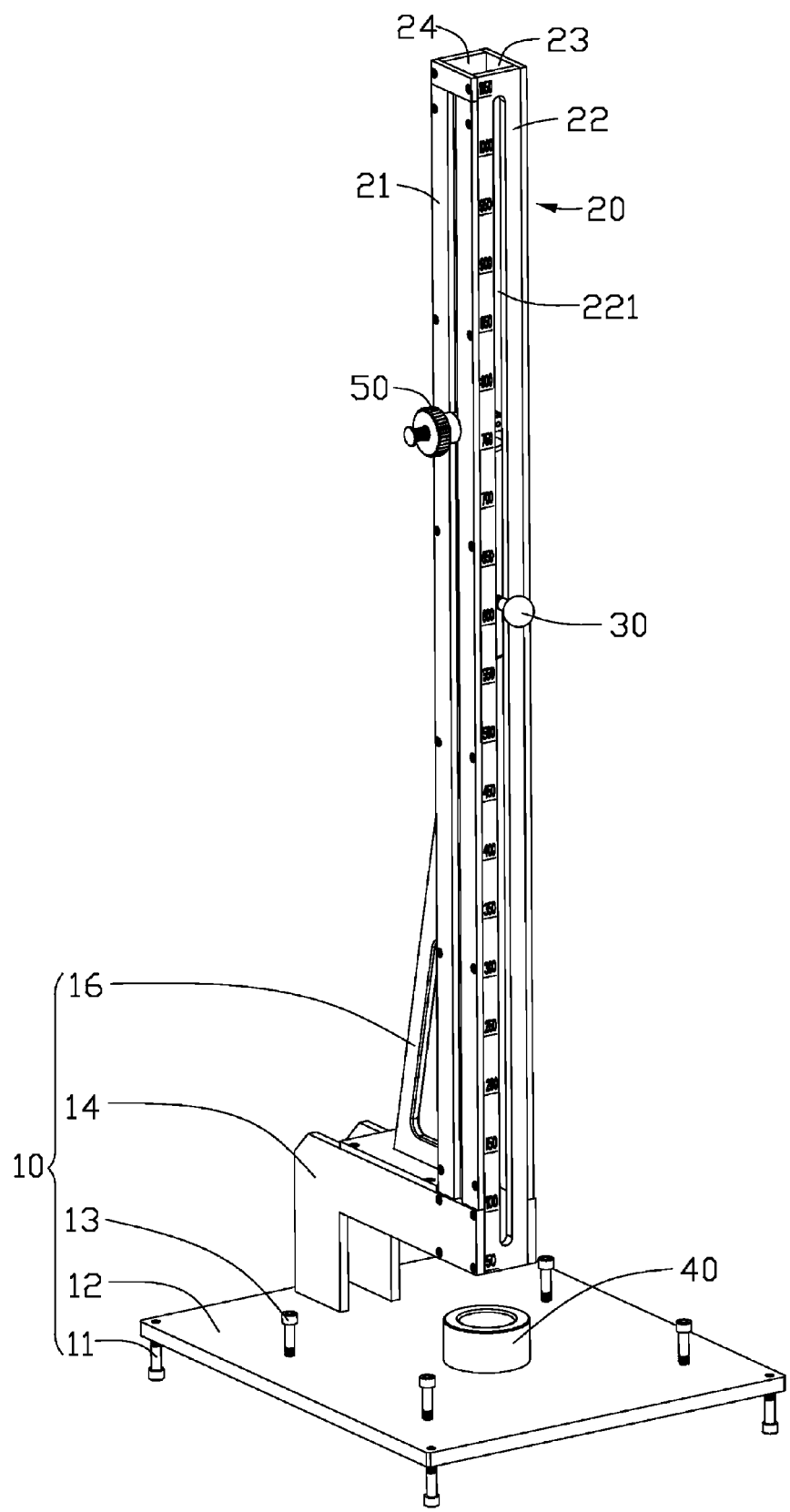
FIG. 1 is an assembled, isometric view of an exemplary embodiment of an impact testing apparatus.
Figure 2:
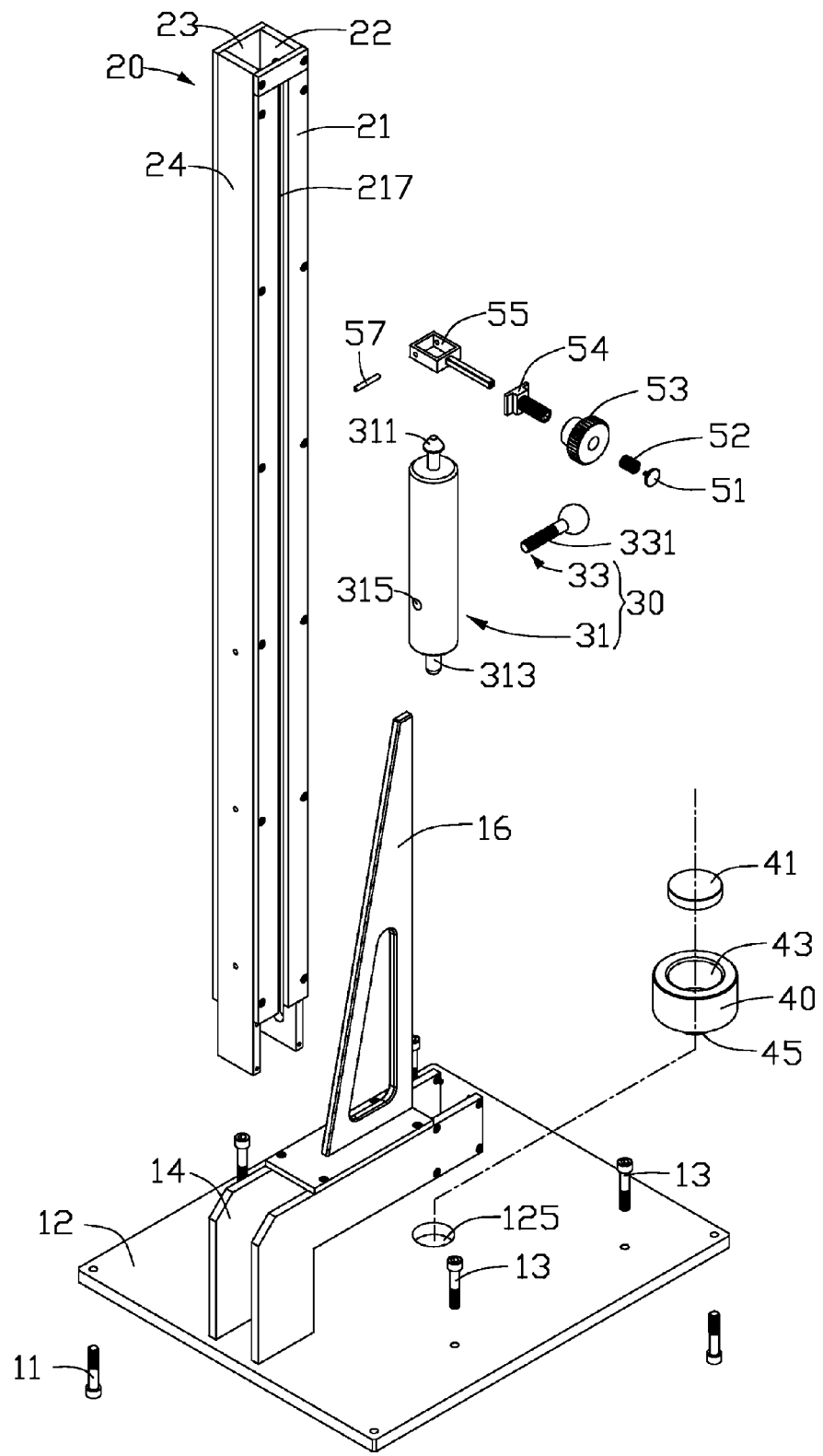
FIG. 2 is an exploded, isometric view of the impact testing apparatus of FIG. 1, the impact testing apparatus including a fastening mechanism.

Referring to FIGS. 1 and 2, an exemplary embodiment of an impact testing apparatus includes a workbench 10, a bracket 20, a hammer 30, an anvil 40, and a fastening mechanism 50.

The workbench 10 includes a horizontal platform 12, a plurality of supporting bolts 11 screwed in four corners of the platform 12 to support the platform, an L-shaped connecting member 14 extending up from the platform 12, and a triangle-shaped reinforcing member 16 extending up from the connecting member 14. The connecting member 14 includes a vertical part and a horizontal part perpendicularly extending from a first end of the vertical part. A second end of the vertical part is perpendicularly mounted to the platform 12. Thus, the horizontal part is parallel to the platform 12. A positioning hole 125 is defined in the middle of the platform 12 under the horizontal part of the connecting member 14. A plurality of retaining posts 13 extends up from the platform 12, surrounding the positioning hole 125. A plurality of screw holes (not shown) is defined in a vertical side of the reinforcing member 16.

The bracket 20 is a hollow long bar having a square cross section. A passage is defined in the bracket 20 along the longitudinal axis of the bracket 20. The bracket 20 includes a first sidewall 21, a second sidewall 23 opposite to the first sidewall 21, a third sidewall 22 perpendicularly connected between corresponding ends of the first and second sidewalls 21 and 23, and a fourth sidewall 24 opposite to the third sidewall 22. A first slot 217 is longitudinally defined in the first sidewall 21, through a bottom of the first sidewall 21. A second slot 221 is longitudinally defined in the second sidewall 23. A plurality of apertures 241 is defined in the fourth sidewall 24, corresponding to the plurality of screw holes of the reinforcing member 16.

The hammer 30 includes a cylindrical body 31 and a handle 33. A holding portion 311 and an attacking pole 313 respectively extend from opposite ends of the body 31. The holding portion 311 is mushroom-shaped, and includes a small end connected to the body 31 and a taper-shaped head opposite to the small end. The body 31 defines a screw hole 315 therein. The handle 33 includes a threaded shank 331 to engage in the screw hole 315.

The anvil 40 is cylindrical and defines a receiving hole 43 along an axis direction. The anvil 40 forms a positioning post 45 at a closed end opposite to the receiving hole 43, to be fixed in the positioning hole 125 of the platform 10. A cushion 41 is received in the receiving hole 43 of the anvil 40.

Figure 3:
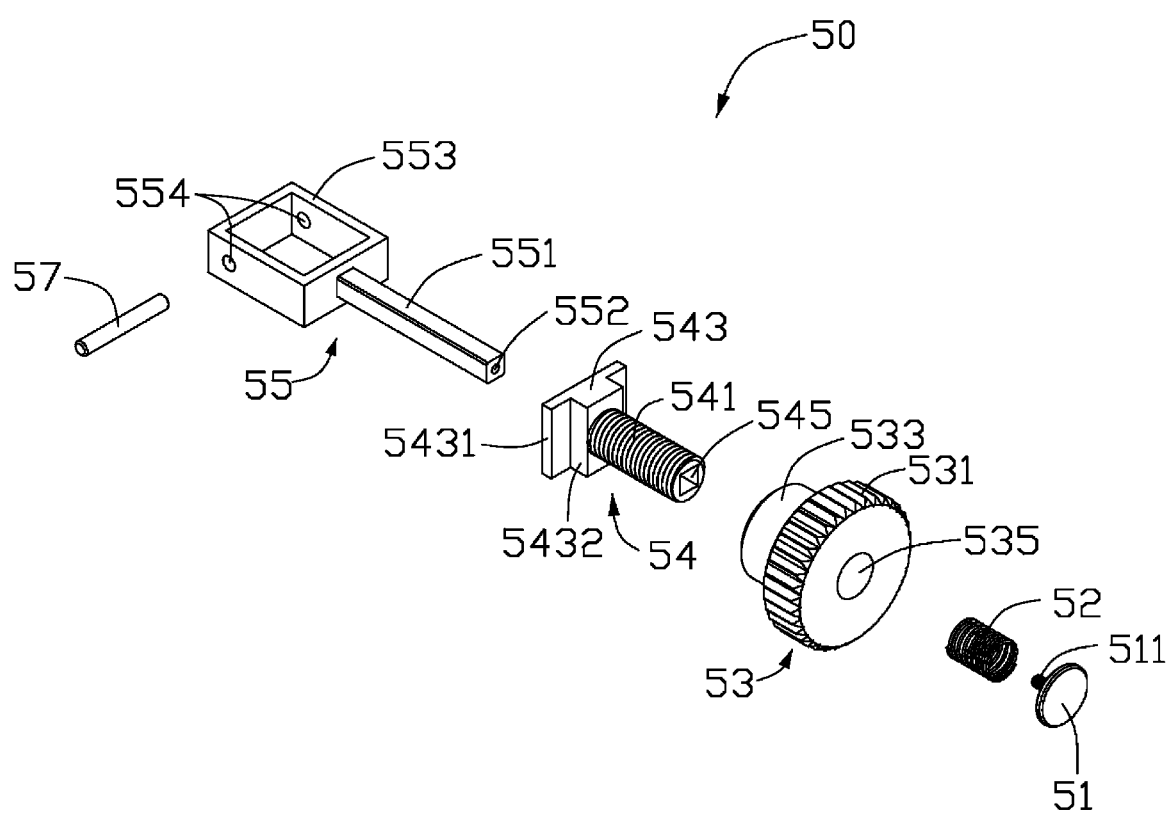
FIG. 3 is an enlarged view of the fastening mechanism of FIG. 2.

Referring to FIG. 3, the fastening mechanism 50 includes a button 51, a coil spring 52, a knob 53, a sliding member 54, a retaining member 55, and a pin 57. The button 51 includes a securing portion 511. The knob 53 includes a manipulating portion 531 and an abutting portion 533 extending from a side of the manipulating portion 531. A screw hole 535 is defined in the knob 53 through the manipulating portion 531 and the abutting portion 533. The sliding member 54 includes a T-shaped sliding block 543 and a threaded shank 541. The sliding block 543 includes a greater blocking portion 5431 and a smaller sliding portion 5432 extending from a side of the blocking portion 5431. The threaded shank 541 extends from the sliding portion 5432, away from the blocking portion 5431. A through hole 545 is defined in the sliding member 54, through the threaded shank 541 and the sliding block 543. The retaining member 55 includes a rectangular frame 553 and a connecting pole 551. The frame 55 includes a first sidewall (not labeled), and two second sidewalls (not labeled) perpendicularly connected to opposite ends of the first sidewall. The connecting pole 551 perpendicularly extends from the first sidewall of the frame 553. Two fixing holes 554 aligning with each other are defined in the two second sidewalls of the frame 553, to hold the pin 57. The connecting pole 551 defines a securing hole 552 in a distal end opposite to the frame 553.

Figure 4:
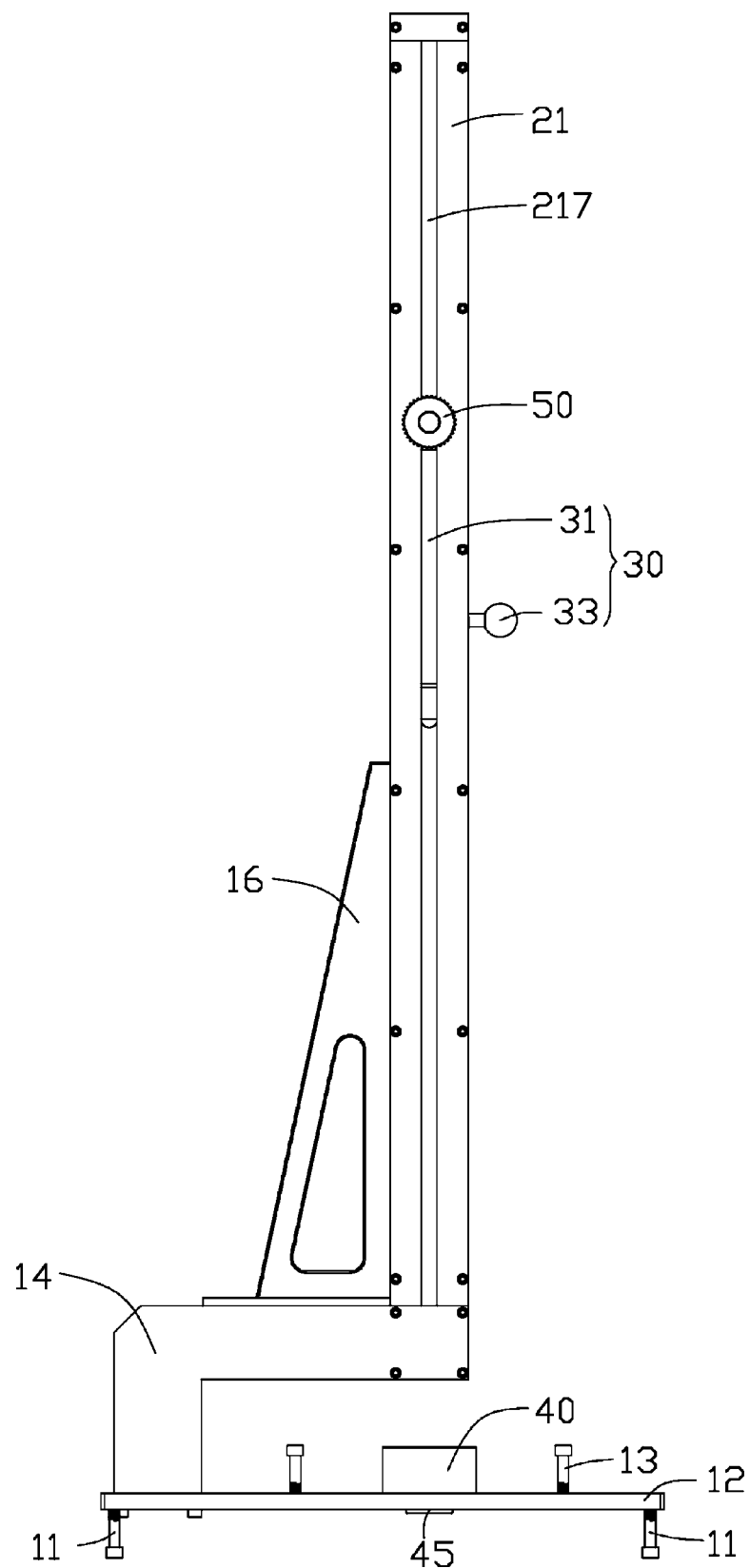
FIG. 4 is a left-side elevational view of the impact testing apparatus of FIG. 1.
Figure 5:
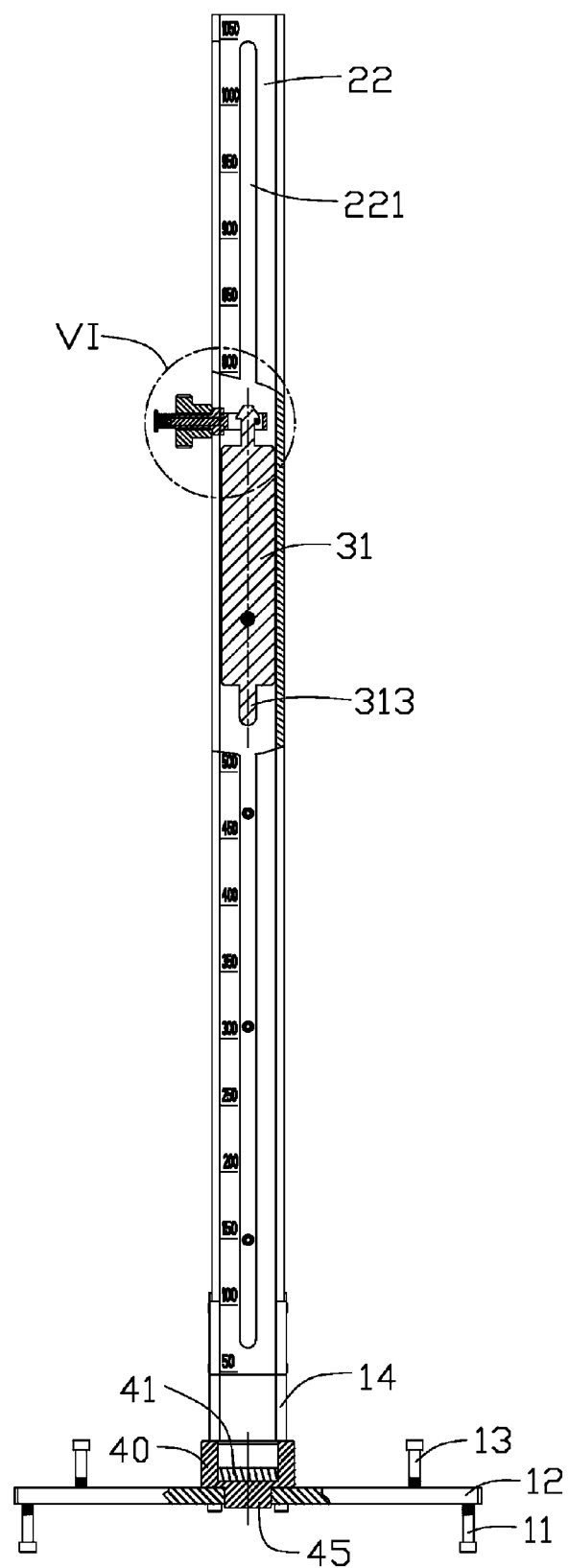
FIG. 5 is a front elevational, partially cutaway view of the impact testing apparatus of FIG. 1.
Figure 6:
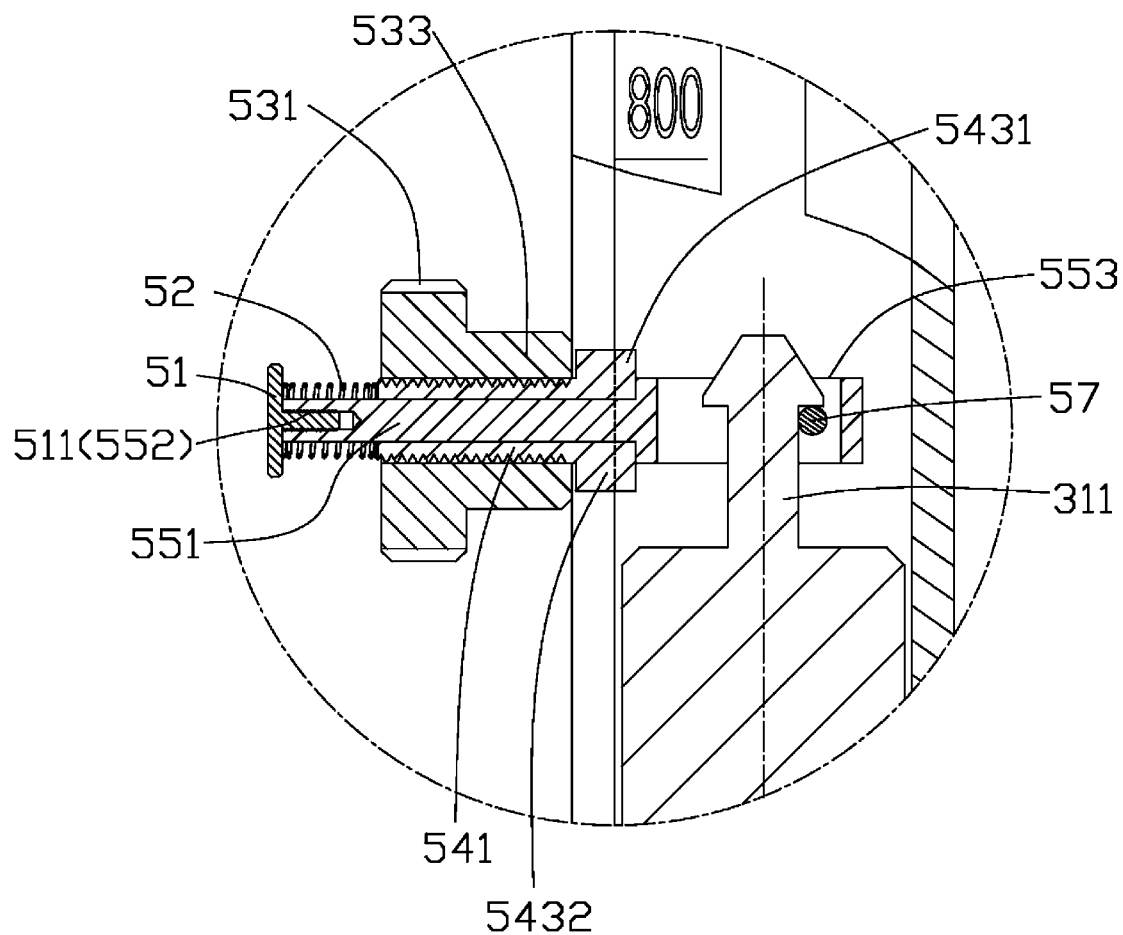
FIGS. 6 and 7 are enlarged views of the encircled portion VI of FIG. 5, but showing two different states.

Referring to FIGS. 4 to 6, in assembly, the pin 57 is engaged in the fixing holes 554 of the frame 553 of the retaining member 55. The connecting pole 551 slidably passes through the through hole 545 of the sliding member 54 from the sliding block 543. The frame 553 of the retaining member 55 and the sliding block 543 of the sliding member 54 are received in the passage of the bracket 20 from a bottom of the bracket 20. The sliding portion 5432 of the sliding member 54 slides in the first slot 217, and the blocking portion 5431 located at opposite sides of the sliding portion 5432 abuts against an inside surface of the first side wall 21 of the bracket 20. The threaded shank 541 extends out of the bracket 20 through the first slot 217 and engages in the screw hole 535 of the knob 53 by rotating the knob 53, until the abutting portion 533 abuts against an outside surface of the first wall 21 of the bracket 20. Therefore, the sliding member 54 is stopped from sliding along the first wall 21. The connecting pole 551 further extends out of the manipulating portion 531 through the screw hole 535 of the knob 53, and passes through the coil spring 52. The securing portion 511 of the button 50 is fixed in the securing hole 552 of the connecting pole 551 of the retaining member 55, therefore, opposite ends of the coil spring 52 resist against the manipulating portion 531 of the knob 53 and the button 51.

The body 31 of the hammer 30 is vertically received in passage of the bracket 20 from the bottom of the bracket 20 and under the fastening mechanism 50, with the attacking pole 313 extending downwards. The threaded shank 331 of the handle 33 passes through the second slot 221 of the bracket 20 and is screwed in the screw hole 315 of the body 31. The hammer 30 is capable of being lifted up or put down, by sliding the handle 33 along the second slot 221. When the holding portion 311 resists against the pin 57, the retaining member 55 is pushed to drive the button 51 to move towards the knob 53, such that the coiling spring 52 is deformed. When the taper-shaped head of the holding portion 311 moves over the pin 57, the coiling spring 52 restores and biases the button 51 away from the knob 53. The retaining member 55 and the pin 57 is moved with the button 51, therefore, the pin 57 engages with a bottom of the holding portion 311 of the body 31 of the hammer 30, to retain the hammer 30 in the bracket 20.

The anvil 40 is secured to the platform 12 of the workbench 10 by fixing the positioning post 45 in the positioning hole 125. The cushion 41 is placed in the receiving hole 43 of the anvil 40.

The bottom of the bracket 20 is secured to a distal end of the horizontal part of the connecting member 14 via a plurality of screws, away from the vertical part of the connecting member 14. The vertical lateral of the reinforcing member 16 abutting against the fourth sidewall 24 of the bracket 20, a plurality of screws pass through the second slot 221 and the apertures 241 of the fourth sidewall 24, and then engage into the corresponding screw holes of the vertical lateral of the reinforcing member 16. Therefore, the bracket 20 is vertically fixed to the workbench 10 and an axis of the body 31 of the hammer 30 aligns with an axis of the anvil 40.

Figure 7:
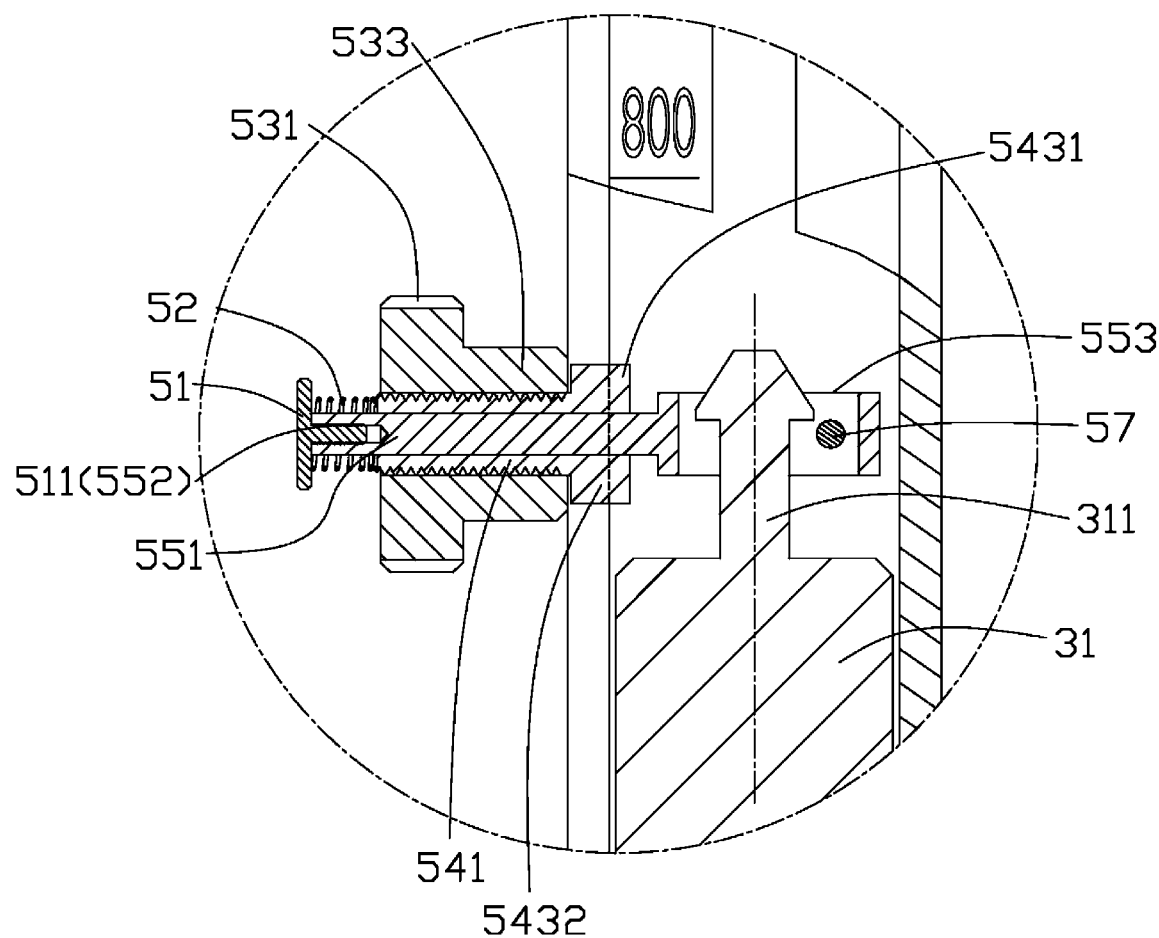
Figure 8:
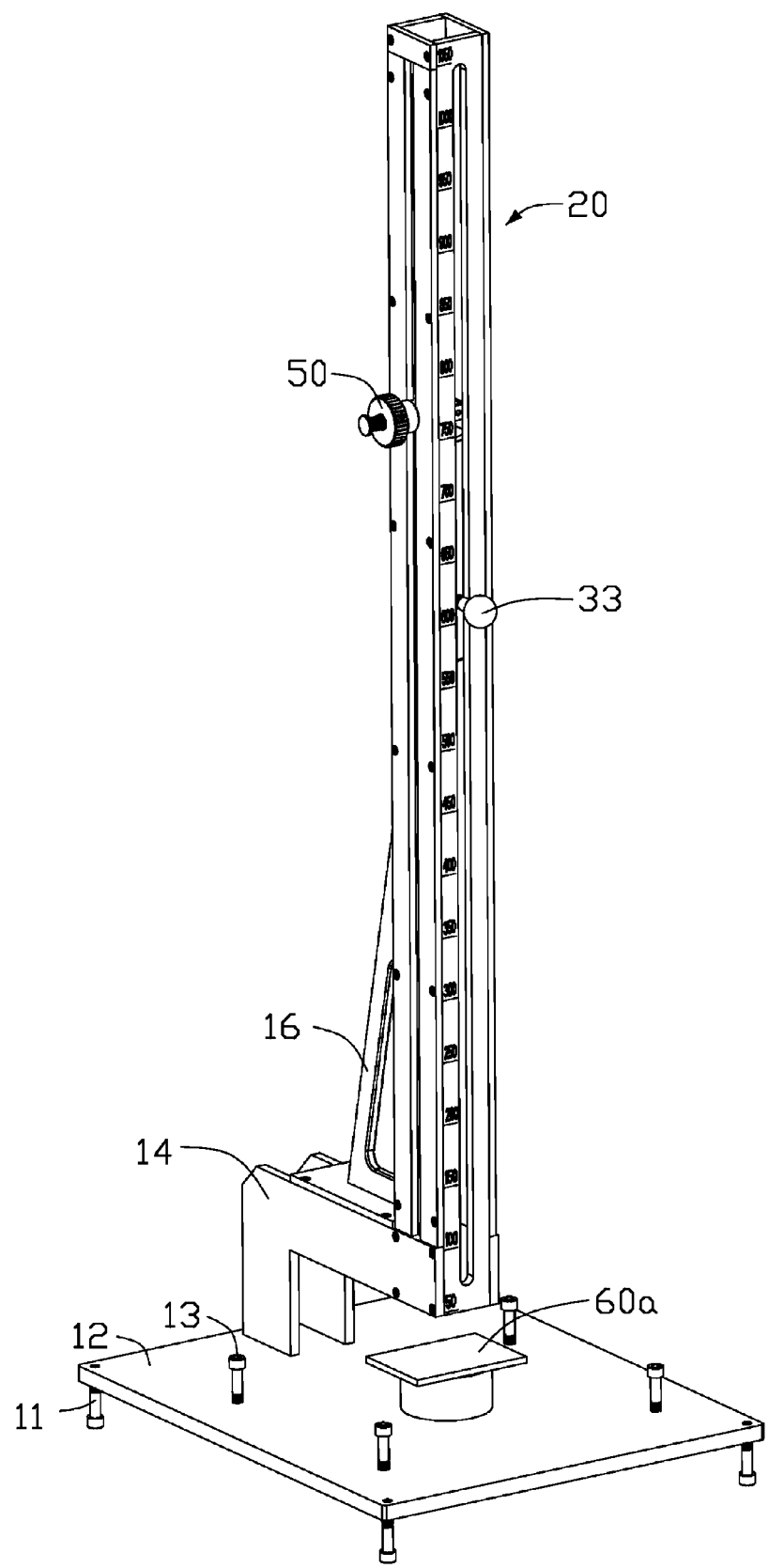
FIG. 8 is similar to FIG. 1, but showing with a workpiece to be tested.

Referring to FIGS. 7 and 8, in use, a workpiece 60*a* having a small size may be placed on the anvil 40, covering the receiving hole 43. The manipulating portion 531 is rotated to release the sliding member 54 from the first side wall 21 of the bracket 20. The fastening mechanism 50 is adjusted to a predetermined height, with the sliding portion 5432 sliding in the first slot 217. The manipulating portion 531 is reversely rotated to fix the fastening mechanism 50 together with the hammer 30 at the predetermined height. The button 51 is driven to move towards the knob 53 to deform the coiling spring 52. The retaining member 55 is moved with the button 51, resulting in the holding portion 311 of the hammer 30 disengaging from the pin 57. Therefore, the hammer 30 falls from the predetermined height, and the attacking pole 313 of the hammer 30 impacts the workpiece 60*a*. In case the workpiece 60*a* is broken by the falling hammer 30. The cushion 41 received in the receiving hole 43 of the anvil 40 can protect the attaching pole 313 from being damaged by directly knocking at the closed end of the anvil 40.

Figure 9:
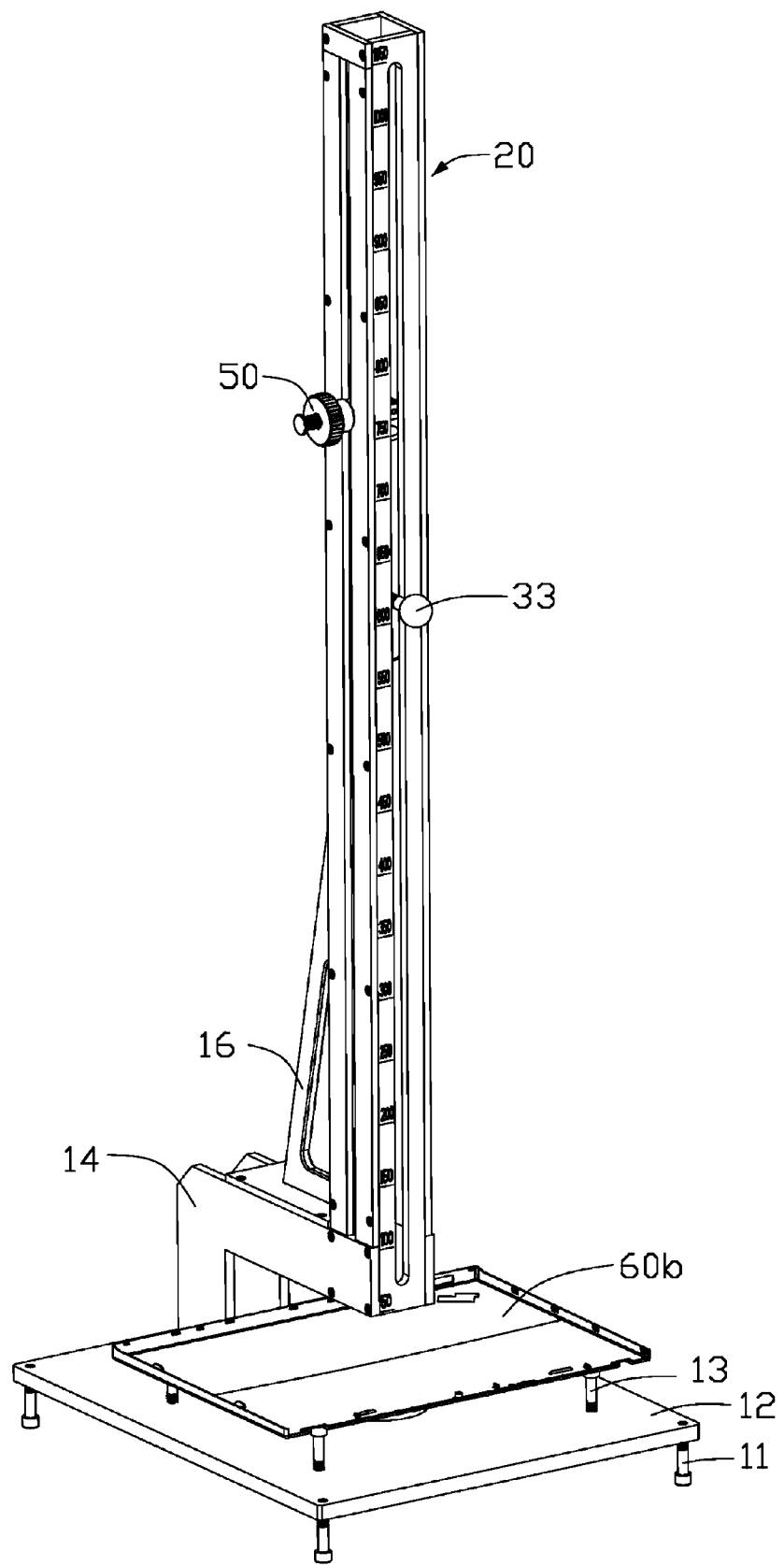
FIG. 9 is similar to FIG. 8, but showing with a different workpiece to be tested.

Referring to FIG. 9, when a workpiece 60*b* having a greater size needs to be tested, the workpiece 60*b* is placed on the anvil 40, and supported by the retaining posts 13. The retaining posts 13 can be adjusted to assure the top of the retaining posts 13 and the anvil 40 are coplanar, therefore, the workpiece 60*b* abuts against the anvil 40 in balance to increase the accuracy of the testing result.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A testing apparatus for performing an impact test for a workpiece, the testing apparatus comprising:
   a workbench comprising a horizontal platform and a connecting member extending up from the platform;
   a bracket arranged over the platform and connected to the connecting member, the bracket defining a vertical passage;
   a hammer slidably received in the passage of the bracket;
   a fastening mechanism slidably mounted to the bracket to be selectively fixed to different heights of the bracket relative to the platform, wherein the fastening mechanism comprises a retaining member capable of being biased between a fist position to hold the hammer and a second position to release the hammer; and
   an anvil disposed on the platform and aligned with the passage, configured for supporting the workpiece;
   wherein the bracket comprises a first sidewall, the fastening mechanism further comprises:
   a sliding member comprising a sliding block slidably received in the passage of the bracket and abutting against an inside surface of the first sidewall of the bracket; and
   a knob engaging with the sliding member and abutting against an outside of the first sidewall of the bracket;
   wherein the knob is capable of being adjusted to move toward the sliding member to snuggly sandwich the first sidewall of the bracket, or to move away from the sliding member to release the first sidewall of the bracket;
   wherein the fastening mechanism further comprises a retaining member and a connecting pole extending from the retaining member, the retaining member comprises a frame received in the passage of the bracket, to engage with or disengage from the hammer, the connecting pole passes through the sliding member and the knob.

2. The testing apparatus of claim 1, wherein the first sidewall of the bracket vertically defines a first slot; the sliding block is T-shaped and comprises a smaller sliding portion sliding in the first slot of the bracket and a greater blocking portion abutting against an inside surface of the first sidewall of the bracket.

3. The testing apparatus of claim 2, wherein the sliding member further comprises a threaded shank extending from the sliding portion opposite to the blocking portion, the threaded shank extends out of the first sidewall of the bracket through the first slot; the knob defines a screw hole to screwably engage with the threaded shank of the sliding member, to move toward or away from the sliding member.

4. The testing apparatus of claim 1, wherein the fastening mechanism further comprises a pin secured to the frame of the retaining member, the hammer comprises a body, and a mushroom-shaped holding portion connected to the body and capable of being held by the pin.

5. The testing apparatus of claim 4, wherein the frame is rectangular and comprises a first sidewall and two opposite second sidewalls perpendicularly connected to corresponding ends of the first sidewall of the frame, the connecting pole extends from the first sidewall, the pin is fixed to the second sidewalls of the frame.

6. The testing apparatus of claim 4, wherein the hammer further comprises an attaching pole opposite to the holding portion, configured for impacting the workpiece.

7. The testing apparatus of claim 4, wherein the bracket further comprises a second sidewall perpendicularly connected to the first sidewall, the second sidewall vertically defines a second slot, the hammer further comprises a handle passing through the second slot to be connected to the body of the hammer.

8. The testing apparatus of claim 1, wherein the fastening mechanism further comprises a button, a distal end of the connecting pole exposes out of the knob, the button is fixed to the distal end, to prevent the retaining member from disengaging from the knob.

9. The testing apparatus of claim 8, wherein the fastening mechanism comprises a coil spring placed around the connecting pole of the retaining member, opposite ends of the coiling spring resist against the knob and the button.

10. The testing apparatus of claim 1, wherein the workbench further comprises a reinforcing member, the reinforcing member comprises a horizontal side abutting against the connecting member of the workbench, and a vertical side abutting against the bracket.

11. The testing apparatus of claim 1, further comprising a cushion, wherein the anvil defines a receiving hole aligning with the passage of the bracket, for receiving the cushion.

12. A testing apparatus for performing an impact test for a workpiece, the testing apparatus comprising:

a workbench configured for supporting the workpiece;

a bracket located above the workbench and comprising a sidewall bounding a through hole aligning with the workpiece, the sidewall vertically defining a slot having a top end and a bottom end;

a hammer vertically received in the through hole of the bracket to free-fall along the bracket; and a retaining member received in the through hole of the bracket and capable of engaging with the hammer to hang the hammer, or disengaging from the hammer resulting in the hammer falling down in the through hole to impact the workpiece, wherein the retaining member comprises a connecting pole extending out of the bracket through the slot, the connecting pole is operable to be fixed to the sidewall of the bracket at any position between the top end and the bottom end of the slot;

wherein the retaining member comprises a frame, a connecting pole extending from the frame, an elastic member fitting about the connecting pole, and a button; wherein the frame is received in the through hole of the bracket, a distal end of the connecting pole opposite to the frame extends out of the bracket through the slot of the sidewall of the bracket, the button is mounted to the distal end to sandwich the elastic member between the button and the sidewall of the bracket.

13. The testing apparatus of claim 12, wherein the hammer comprises a holding portion at a top end and an attacking portion at a bottom end, the holding portion is capable of driving the retaining member to move to make the holding portion move above the retaining member then engage with the retaining member in response to the retaining member restoring, the attacking portion is configured for impacting the workpiece after the hammer disengages from the retaining member to fall down.

* * * * *